United States Patent
Hwang et al.

(10) Patent No.: US 9,568,519 B2
(45) Date of Patent: Feb. 14, 2017

(54) BUILDING ENERGY CONSUMPTION FORECASTING PROCEDURE USING AMBIENT TEMPERATURE, ENTHALPY, BIAS CORRECTED WEATHER FORECAST AND OUTLIER CORRECTED SENSOR DATA

(71) Applicant: International Business Machines Corporation, Armonk, NY (US)

(72) Inventors: Youngdeok Hwang, White Plains, NY (US); Young Min Lee, Old Westbury, NY (US); Yada Zhu, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 450 days.

(21) Appl. No.: 14/278,603

(22) Filed: May 15, 2014

(65) Prior Publication Data
US 2015/0331023 A1    Nov. 19, 2015

(51) Int. Cl.
*G06F 19/00*     (2011.01)
*G01R 21/133*    (2006.01)
*G01N 25/20*     (2006.01)
*G06Q 10/04*     (2012.01)
*G06Q 50/06*     (2012.01)

(52) U.S. Cl.
CPC ............ *G01R 21/133* (2013.01); *G01N 25/20* (2013.01); *G06Q 10/04* (2013.01); *G06Q 50/06* (2013.01)

(58) Field of Classification Search
CPC .. G01D 4/004; G01R 19/2506; G05B 19/0428
USPC ............... 702/60, 64–66, 182–185
See application file for complete search history.

(56) References Cited

U.S. PATENT DOCUMENTS

| | | | |
|---|---|---|---|
| 7,200,468 B2 | 4/2007 | Ruhnke et al. | |
| 7,216,021 B2 | 5/2007 | Matsubara et al. | |
| 8,078,330 B2 | 12/2011 | Brickfield et al. | |
| 8,140,193 B2 | 3/2012 | Lee | |
| 8,321,188 B2 | 11/2012 | Johnson et al. | |
| 8,370,283 B2 | 2/2013 | Pitcher et al. | |
| 8,495,886 B2 | 7/2013 | Singh et al. | |
| 8,554,384 B2 | 10/2013 | West et al. | |
| 2003/0061091 A1 | 3/2003 | Amaratunga et al. | |

(Continued)

OTHER PUBLICATIONS

Kissock, J. K., et al., "Inverse Model Toolkit: Numerical Algorithms", ASHRAE Transaction, VBDD (Variable Base Degree Day) model with Static Data, pp. 425-434, vol. 109, Part 2, Published by: Amer. Soc. Heating, Ref. Air-Conditoning Eng. Inc., Conference: ASHRAE Transactions Technical and Symposium Papers, Kansas City, MO.

(Continued)

*Primary Examiner* — Edward Raymond
(74) *Attorney, Agent, or Firm* — Scully, Scott, Murphy & Presser, P.C.; Daniel P. Morris, Esq.

(57) ABSTRACT

A procedure for forecasting building energy consumption by evaluating performance of variable base degree and variable based enthalpy models. Dynamic weights are computed for the variable base degree and variable based enthalpy models and used in making future energy prediction based on weather forecast data. The weather forecast data may be corrected for bias. The variable base degree and variable based enthalpy models may be calibrated based on outlier removed historic energy consumption data and historic ambient air temperature data.

20 Claims, 8 Drawing Sheets

(56) References Cited

U.S. PATENT DOCUMENTS

| | | | |
|---|---|---|---|
| 2004/0102937 A1 | 5/2004 | Ibrahim | |
| 2011/0251726 A1* | 10/2011 | McNulty | G05B 13/0265 |
| | | | 700/278 |
| 2012/0084063 A1 | 4/2012 | Drees et al. | |
| 2012/0150707 A1 | 6/2012 | Campbell et al. | |
| 2012/0278051 A1 | 11/2012 | Jiang et al. | |
| 2012/0290230 A1* | 11/2012 | Berges Gonzalez ... | G01D 4/004 |
| | | | 702/61 |
| 2012/0330626 A1 | 12/2012 | An et al. | |
| 2013/0035794 A1 | 2/2013 | Imani | |
| 2015/0248118 A1* | 9/2015 | Li | G05B 13/04 |
| | | | 700/295 |

OTHER PUBLICATIONS

IBM, "Forecasting Energy Consumption of Buildings with Effective Heat Capacities of Heating and Cooling", Aug. 11, 2009, Database: IP.com; IP.com No. IPCOM000186154D, p. 1.

Korolija I., et al., "Regression models for predicting UK office building energy consumption from heating and cooling demands", Energy and Buildings (Energy Build.), Apr. 2013, pp. 214-227, Publisher: Elsevier Ltd., Country of Publication: UK.

* cited by examiner

BUILDING ENERGY CONSUMPTION FORECASTING PROCEDURE USING AMBIENT TEMPERATURE, ENTHALPY, BIAS CORRECTED WEATHER FORECAST AND OUTLIER CORRECTED SENSOR DATA

FIELD

The present application relates generally to energy consumption and more particularly to predicting energy consumption in a building, computer-implemented methods and systems for predicting energy consumption in a building.

BACKGROUND

Many commercial buildings have meters and sub-meters that measure energy consumption in various zones of a building and for various equipment, e.g., chillers, boilers, pumps, air handling unit (AHU), lighting, plug load, etc. Such meters and sub-meters can provide high resolution meter data (e.g., by 15-minutes and hourly, etc.) and a computerized system such as a Building Management System (BMS) stores such meter data, making them readily available.

A known system develops a regression model (Variable Base Degree, VBD model) that correlates the building energy consumption with heating degree load (positive difference between a reference temperature and outside temperature at each time period, e.g., heating degree day in a month) and cooling degree load (negative difference between a reference temperature and outside temperature at each time period, e.g., cooling degree day in a month) for predicting energy consumption based on weather forecast.

BRIEF SUMMARY

A method of predicting energy consumption in a building, in one aspect, may comprise receiving historic ambient air data. The method may also comprise receiving historic energy consumption data associated with a building. The method may further comprise calibrating a variable base degree model based on the historic ambient air data and the historic energy consumption data. The method may also comprise calibrating a variable based enthalpy model based on the historic ambient air data and the historic energy consumption data. The method may also comprise receiving weather forecast data. The method may also comprise running the variable base degree model with the weather forecast data to produce a first energy consumption prediction. The method may further comprise running the variable based enthalpy model with the weather forecast data to produce a second energy consumption prediction. The method may also comprise computing a first weight associated with the variable base degree model dynamically based on performance of the variable base degree model and performance of the variable based enthalpy model during a predefined time period. The method may also comprise computing a second weight associated with the variable based enthalpy model dynamically based on performance of the variable based enthalpy model and the variable base degree model during the predefined time period. The method may further comprise combining the first energy consumption prediction and the second energy consumption prediction as a function of the first weight and the second weight.

A system for predicting energy consumption in a building, in one aspect, may comprise a processor. The system may also comprise a variable base degree model calibrated by the processor based on historic ambient air data and historic energy consumption data. The system may also comprise a variable based enthalpy model calibrated based on the historic ambient air data and the historic energy consumption data. The processor may be operable to receive weather forecast data and run the variable base degree model with the weather forecast data to produce a first energy consumption prediction. The processor may be further operable to run the variable based enthalpy model with the weather forecast data to produce a second energy consumption prediction. The processor may be further operable to compute a first weight associated with the variable base degree model dynamically based on performance of the variable base degree model and the variable based enthalpy model during a predefined time period. The processor may be further operable to compute a second weight associated with the variable based enthalpy model dynamically based on performance of the variable based enthalpy model and the variable base degree model during the predefined time period. The processor may be further operable to combine the first energy consumption prediction and the second energy consumption prediction as a function of the first weight and the second weight.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

In buildings, forecasted energy consumption information can be used to plan energy supply (e.g., grid electricity purchase from spot market and day ahead market), and energy demand (e.g., distribute the energy load in different ways, and shave or shift peak energy consumption). Also, predicted energy consumption can be compared with actual measured energy consumption to detect anomaly (out of control bound, drifting trends) and faults of energy consuming equipment or devices in buildings. Therefore, accurately predicting energy consumption in a building is useful.

An approach is presented that predicts energy consumption of buildings. The approach in one embodiment combines Variable Base Degree (VBD) and Variable Based Enthalpy (VBE) models in dynamically weighted manner with bias corrected weather forecast data and outlier corrected sensor data.

In one embodiment of the present disclosure, calibration performance of VBD and VBE are evaluated and weighted forecasts of VBD and VBE models are used for energy consumption forecast. Outlier data in the historic data of energy consumption and ambient weather conditions are identified and removed for the calibration of VBD and VBE model. Bias of weather forecast is identified with a regression model with temporal variables by comparing historic weather forecast data and corresponding building ambient sensor data, and corrected to be used for VBD and VBE model.

Figure 1:
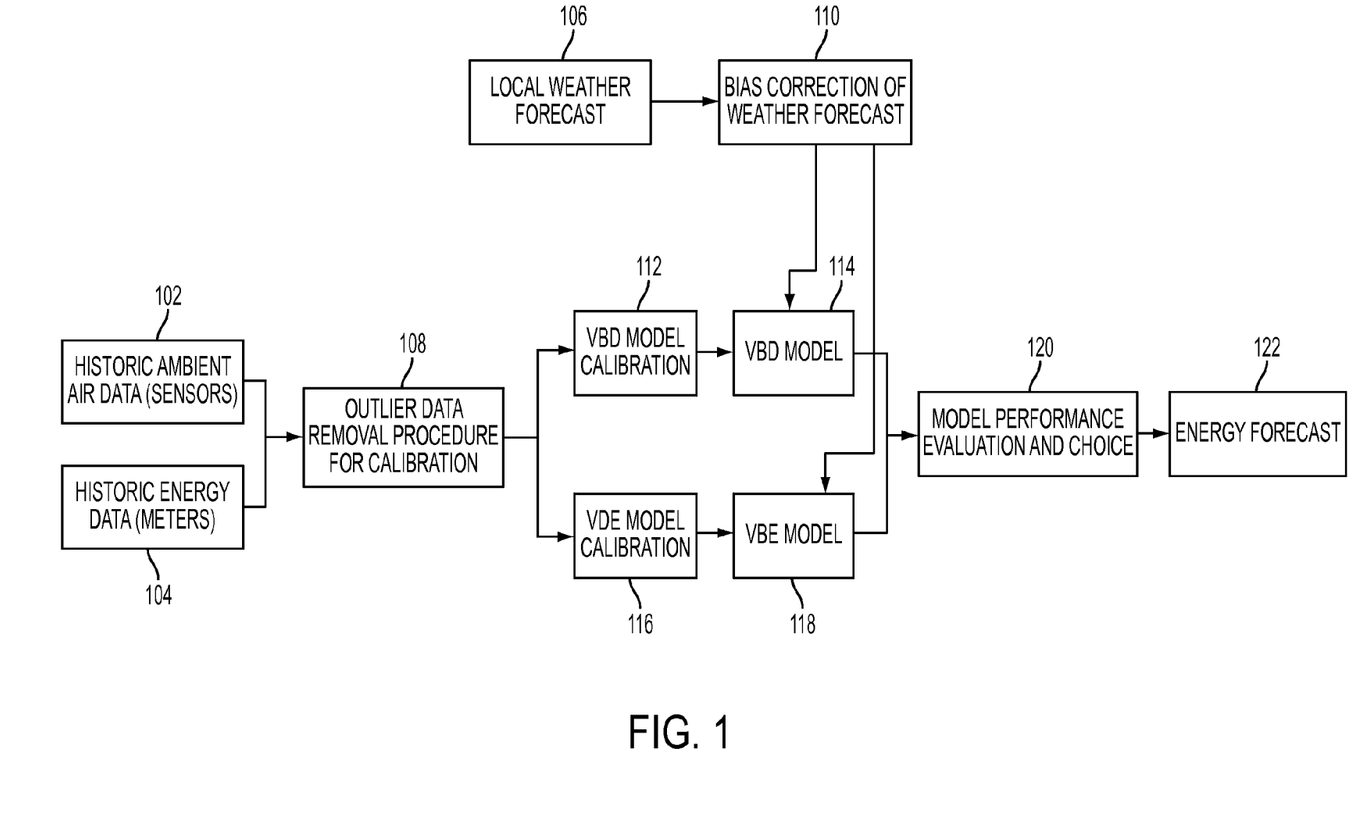
FIG. 1 is a diagram illustrating an overview of an energy consumption prediction methodology in one embodiment of the present disclosure.

FIG. 1 is a diagram illustrating an overview of an energy consumption prediction methodology in one embodiment of the present disclosure. Blocks 102, 104 and 106 represent inputs to the methodology. Block 122 represents an output of the methodology.

Historic ambient air data 102, for example, recorded by sensors, may be obtained. Historic energy consumption data, measured by meters installed in a building, may be obtained. This data shows how much energy was consumed in a building, in a section of a building, or by equipment in a building, based on the meter measurement.

At 108, outlier data from the historic ambient air data 102 and historic energy data 104 is detected and removed. The historic ambient air data and the historic energy data with outlier data removed are used for VBD model calibration 112 and also VBE model calibration 116. The model calibration at 112 estimates parameters of a VBD model and produces a VBD model 114; the model calibration at 116 estimate parameters of a VBE model and produces a VBE model 118. Given weather forecast data, e.g., if weather forecast (ambient temperature) is available, the VBD model 114 can predict energy consumption for the future time corresponding to the time period of the weather forecast. The VBE model 118 can predict energy consumption for the future time corresponding to the time period of the weather forecast, given the weather forecast data (ambient enthalpy, h). Enthalpy can be computed from outdoor ambient temperature, and outdoor humidity (%).

As shown at 106, the weather forecast data is obtained for the future time period for which energy consumption is to be predicted e.g., for next 24 hours. A methodology of the present disclosure in one embodiment may perform bias correction of the weather forecast as shown at 110. The bias corrected weather forecast data is then used in the VBD model 116 and VBE model 118 to predict energy consumption. Both the VBD model 114 and the VBE model 118 predict the energy consumption for the same future time period associated with the obtained weather forecast data.

The VBD model 114 can predict energy consumption of future time if weather forecast (e.g., ambient temperature) is available. VBD (Variable Base Degree) Model 114 may incorporate the following factors in predicting energy consumption.

Degree Day model (DD model), e.g.,
  HDD (Heating Degree Day) Model
    Monthly sum of daily heating degree day
  CDD (Cooling Degree Day) Model
    Monthly sum of daily cooling degree day
Variable Base Degree (VBD) Model
  VBDD (Variable Base Degree Day), VBDH (Variable Based Degree Hour)
  $T_{h,bal}$ (balance temperature for heating) is determined optimally
  $T_{c,bal}$ (balance temperature for cooling) is determined optimally
VBD may be formulated as follows:

$$E_{ij} = b_{ij} + h_{ij} \cdot HD_{ij}(T_{h,bal}) + c_{ij} \cdot CD_{ij}(T_{c,bal}) + \varepsilon_{ij}$$

$$HD_i(T_{h,bal}) = \sum_{j=1}^{N_k} \max(T_{h,bal} - T_j, 0),$$

$$CD_{ij}(T_{c,bal}) = \sum_{j=1}^{N_k} \max(T_j - T_{c,bal}, 0),$$

where
i=time period (e.g., a day);
j=a meter;
k=meter reading interval (e.g., 15 minutes);
$N_k$=number of meter readings k in j;
$E_{ij}$=energy consumption recorded by meter j in time period i;
$b_{ij}$=coefficient for base load for meter j in time period i;
$h_{ij}$=coefficient for heating degree load for meter j in time period i;
$c_{ij}$=coefficient for cooling load for meter j in time period i;
$T_{h,bal}$=balance temperature for heating;
$T_{c,bal}$=balance temperature for cooling.
$HD_{ij}$=heating degree of meter j in time period i;
$CD_{ij}$=cooling degree of meter j in time period i;

A Variable Base Enthalpy (VBE) model 118 predicts energy consumption given the weather forecast data that includes ambient enthalpy, h. A VBE model 118 may consider the following factors in predicting energy consumption:
Enthalpy Day Model (ED Model), e.g.,
  HED (Heating Enthalpy Day) Model
    Monthly sum of daily heating enthalpy day
  CED (Cooling Enthalpy Day) Model
    Monthly sum of daily cooling enthalpy day
Variable Base Enthalpy (VBE) Model
  $h_{h,bal}$ (balance enthalpy for heating) is determined optimally
  $h_{c,bal}$ (balance enthalpy for cooling) is determined optimally
A VBE model may be formulated as follows:

$$E_{ij} = b_j + h_j \cdot HE_{ij}(h_{h,bal,j}) + c_j \cdot CE_{ij}(h_{c,bal,j}) + \varepsilon_{ij}$$

$$HE_{ij}(h_{h,bal,j}) = \sum_{k=1}^{N_j} \max(h_{h,bal,j} - h_k, 0),$$

$$CE_{ij}(h_{c,bal,j}) = \sum_{k=1}^{N_j} \max(h_k - h_{c,bal,j}, 0),$$

wherein, i=time period (e.g., a day);

j=a meter (sensor);

k=meter reading intervals (e.g., 15 minutes, wherein k may be a number of consecutive 15 minute intervals);

$N_j$=number of meter readings in j;

$E_{ij}$=energy consumption recorded by meter j in time period i;

$b_j$=coefficient for base enthalpy load for meter j;

$h_j$=coefficient for heating enthalpy load for meter j;

$c_j$=coefficient for cooling enthalpy load for meter j;

$h_{h,bal,j}$=balance enthalpy for heating associated meter j;

$h_{c,bal,j}$=balance enthalpy for cooling associated meter j;

$h_k$=enthalpy of the outside air at time interval k.

$\epsilon_{ij}$=prediction error in energy consumption.

$HE_{ij}$=heating enthalpy of meter j in time period i;

$CE_{ij}$=cooling enthalpy of meter j in time period i;

Building heating and cooling load sources may include conductive heat transfer through the wall, window and roof; Infiltration, and ventilation air entered into the room with moisture content, which contains latent heat; and Internal load, including people, lighting and equipments. Enthalpy is described as follows: Air is a mixture of dry air and water vapor. In atmospheric air, water vapor content varies from 0~3% by mass. The enthalpy of moist and humid air includes: Enthalpy of the dry air (the sensible heat) and Enthalpy of the evaporated water (the latent heat). In order to more accurately predict the cooling and heating load, the latent content should also be incorporated. Enthalpy difference between weather condition and a base enthalpy value captures both the sensible heat and latent heat, therefore the developed enthalpy model may provide another regression model for the energy consumption forecasting and anomaly detection.

The following describes enthalpy calculation in one embodiment of the present disclosure. Enthalpy is computed from weather data: outdoor dry bulb temperature $T_{db}$, outdoor dew point temperature $T_{dew}$, and atmospheric pressure P. Calculation method may comprise the following.

Saturation pressure $P_w$ over ice for the temperature range of −100 to 0 degrees Celsius is given by:

$$\ln P_w = C_1/T_{dew} + C_2 + C_3 T_{dew} + C_4 T_{dew}^2 + C_5 T_{dew}^3 + C_6 T_{dew}^4 + C_7 \ln T_{dew}$$

Saturation pressure $P_w$ over liquid water for the temperature range of 0 to 200 degrees Celsius is given by:

$$\ln P_w = C_8/T_{dew} + C_9 + C_{10} T_{dew} + C_{11} T_{dew}^2 + C_{12} T_{dew}^3 + C_{13} \ln T_{dew}$$

where, $C_1$=−0.56745359

$C_2$=6.3925247

$C_3$=−9.677843e−03

$C_4$=6.2215701e−07

$C_5$=2.0747825e−09

$C_6$=9.4840240e−13

$C_7$=4.1635019

$C_8$=−5.8002206e+03

$C_9$=1.3914993

$C_{10}$=−4.8640239e−02

$C_{11}$=4.1764768e−05

$C_{12}$=−1.4452093e−08

$C_{13}$=6.5459673

Humidity ratio W is given by:

$$W = 0.62198 \frac{P_W}{P - P_W}$$

Enthalpy of the moist air h is given by:

$$h = 1.006 T_{db} + W(2501 + 1.805 T_{db})$$

In one embodiment of the present disclosure, fitting the variable base enthalpy (VBE) model is considered as a constrained optimization problem due to the non-negative constrain on the coefficients. In the present disclosure in one embodiment, a two step analysis is presented for uncertainty quantification. A model selection procedure is first performed, which selects the correct model. Then an inference is drawn based on the selected model. In the first step of the analysis, a model selection procedure may be performed as follows. Depending on whether one or more of are zeroes, the model space may include the following eight different models:

$E_{ij} = \epsilon_{ij}$ $E_{ij} = b_j + \epsilon_{ij}$ $E_{ij} = h_j \cdot HE_{ij}(h_{h,bal,j}) + \epsilon_{ij}$ $E_{ij} = c_j \cdot CE_{ij}(h_{c,bal,j}) + \epsilon_{ij}$ $E_{ij} = b_j + h_j \cdot HE_{ij}(h_{h,bal,j}) + \epsilon_{ij}$ $E_{ij} = b_j + c_j \cdot CE_{ij}(h_{c,bal,j}) + \epsilon_{ij}$ $E_{ij} = h_j \cdot HE_{ij}(h_{h,bal,j}) + c_j \cdot CE_{ij}(h_{c,bal,j}) + \epsilon_{ij}$ $E_{ij} = b_j + h_j \cdot HE_{ij}(h_{h,bal,j}) + c_j \cdot CE_{ij}(h_{c,bal,j}) + \epsilon_{ij}$ Further details of VBE model is described in co-owned, co-pending U.S. patent application Ser. No. 13/930,536, filed on Jun. 28, 2013, entitled "Constructing and Calibrating Enthalpy Based Predictive Model for Building Energy Consumption," the entire content of which is incorporated herein by reference.

Using the bias corrected weather forecast data, the VBD model 114 and the VBE model 118 each produces energy consumption prediction for the period of time corresponding to the weather forecast data.

At 120, the performance of the two models 114, 118 are compared and recent (e.g., past predefined period of time) performance evaluation history is tracked so that weights for the two models 114, 118 can be computed. The performance evaluation, e.g., determines which model more accurately predicted the energy consumption for a given period for a given building, section of a building or equipment in a building. For example, based on the past performance of the two models, a weight is computed for each model.

The outputs of the two models are combined based on the weights assigned to the models based on their performance accuracy. At 122, energy consumption forecast based on the weighted combination of the outputs of the VBD and VBE models are output.

Whether VBD (Variable Base Degree) model or VBE (Variable Base Enthalpy) model is going to forecast energy consumption more accurately may depend on different factors. For example, different heating, ventilation, and air conditioning (HVAC) system control schemes may provide such different factors. For instance, during the hot and humid summer season, a cooling system may consume energy to reduce indoor temperature as well as humidity, in which case, an enthalpy model can produce more accurate prediction; During the heating season, a heating system may consume energy to increase the indoor temperature, but may not be concerned about raising humidity, in which case a degree model can produce more accurate prediction. Other circumstance that may drive the accuracy of the two models may include occupant behavior and tolerance, local government mandates and/or regulations, energy price, and other factors. Furthermore, the better accuracy of one model over another may change over time.

Referring to FIG. 1 at 110, weather forecast (ambient temperature and enthalpy) available in a region may contain bias with respect to building ambient air data (sensored temperature and humidity data) in a building of interest, and the bias corrected weather forecast data can contribute to more accurate energy forecast when they are used for VBD or VBE models.

Referring to FIG. 1 at 108, building ambient air data (sensored temperature and humidity data) that are used for calibrating the VBD and VBE models could contain inaccurate data (outliers) from time to time (e.g., due to outages, system/sensor failures, etc.). VBD and VBE model can forecast energy consumption more accurately if they are calibrated with such outlier corrected data.

Figure 2:
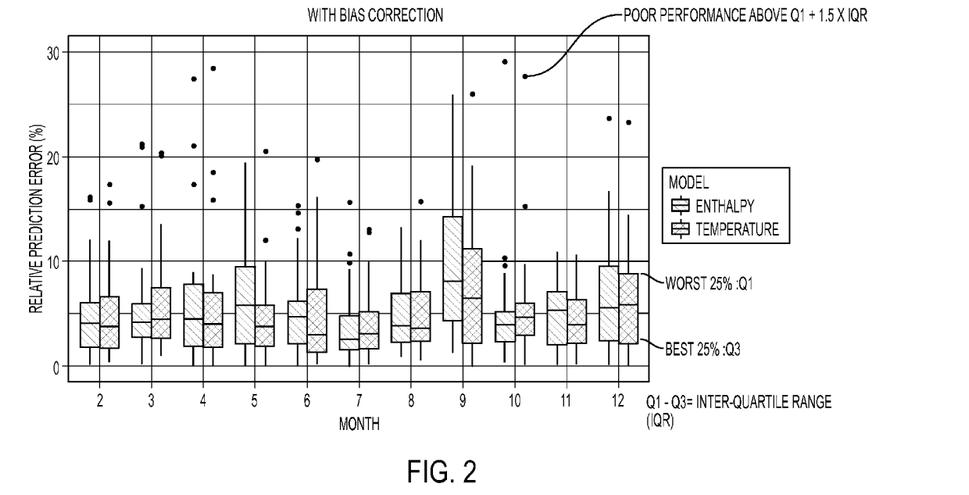
FIG. 2 shows example performance data of VBD and VDE models.

FIG. 2 shows example performance data for the two competing models, VBD and VDE models. The data shows that one model outperforms the other based on the season. The bars shows a range of the relative prediction error with the horizontal line in the bar showing mean prediction error for that model for the specific time period. If this seasonal pattern of two models can be understood and incorporated as part of the prediction algorithm, the prediction performance can be improved. In one embodiment of the present disclosure, such patterns of the models may be incorporated into a prediction algorithm.

For instance, mean absolute percentage error (MAPE) of a model prediction may be computed as follows:

$$MAPE = \frac{100\%}{n} \sum_{t=1}^{n} \frac{|Y_t - \hat{Y}_t|}{Y_t}$$

where, n represents a number of time periods (time period may be in days, hours, etc.);

t represents a time period;

$Y_t$ represents actual meter reading data pertaining to time period t;

$\hat{Y}_t$ represents predicted energy consumption data pertaining to time period t.

TABLE 1

|  | VBD | VBE | Integrated |
|---|---|---|---|
| Feb. | 6.96% | 9.39% | 4.96% |
| Mar. | 8.18% | 11.79% | 5.50% |
| Apr. | 11.38% | 18.95% | 5.55% |
| May | 8.20% | 6.56% | 5.53% |
| Jun. | 6.38% | 6.89% | 4.95% |
| Jul. | 16.23% | 15.62% | 4.02% |
| Aug. | 11.31% | 10.84% | 4.93% |
| Sep. |  |  |  |
| Oct. | 10.02% | 9.82% | 5.25% |
| Nov. | 6.37% | 5.00% | 4.11% |
| Dec. | 7.45% | 8.02% | 6.54% |
| Average | 9.25% | 10.29% | 5.13% |

Table 1 shows example MAPE for time periods ranging from February to December, of VBD model (column 2), VBE model (column 3), and also an integrated model of the present disclosure in (column 4). The formula for computing MAPE above may be used to compute the values shown in the table.

Figure 3:
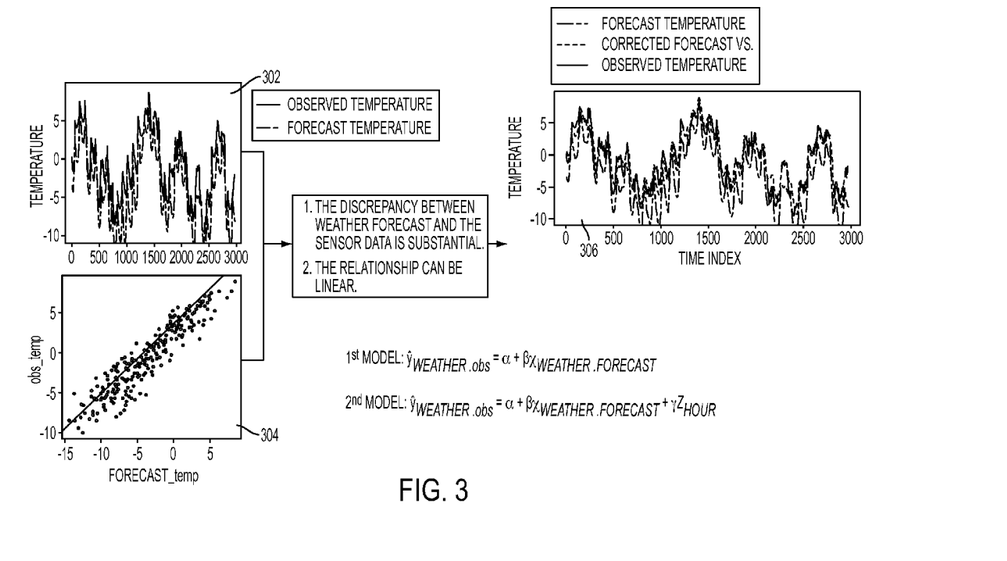
FIG. 3 shows bias correction of weather forecast in one embodiment of the present disclosure.

FIG. 3 shows bias correction of weather forecast in one embodiment of the present disclosure. The graph shown at 302 illustrates that there is a discrepancy between weather forecast and the actual observed data outside a building of interest, which discrepancy may be substantial. A plot 304 of the forecasted temperature for the area of the building with the observed temperature (actual sensor data) shows that the relationship between the two can be linear. Thus, in one embodiment of the present disclosure, the bias correction of weather forecast may be implemented as:

$$\hat{y}_{weather.obs} = \alpha + \beta x_{weather.forecast}$$

where $\hat{y}_{weather.obs}$ represents observed weather data;

$\alpha$ and $\beta$ represent coefficients of a regression model describing the relationship between the observed weather data and the weather forecast data for the same time period. Using the obtained $\alpha$ and $\beta$ parameters, bias in future weather forecast data may be obtained. So, e.g., bias corrected weather forecast may be obtained by solving $\alpha + \beta x_{weather.forecast}$.

In another embodiment of the present disclosure, a weather forecast bias correction model may compensate for time dependent bias (e.g., hourly, daily, etc.). For instance, bias in weather forecast may be different at different times. A bias correction of weather forecast may for example take the form of:

$$\hat{y}_{weather.obs} = \alpha + \beta x_{weather.forecast} + \gamma z_{hour}$$

where $\hat{y}_{weather.obs}$ represents observed weather data;

$\alpha$ and $\beta$ represent coefficients of a regression model describing the relationship between the observed weather data and the weather forecast data for the same time period; and $\gamma z_{hour}$ represents bias difference at different time periods (while $z_{hour}$ is shown, another time period or increment may apply, e.g., $z_{day}$). The $z_{hour}$ is an incidence vector indicating which time interval the corresponding observation belongs to, and $\gamma$ is the corresponding coefficient vector.

So, e.g., in another embodiment, bias corrected weather forecast may be obtained by solving $\alpha + \beta x_{weather.forecast} + \gamma z_{hour}$. The graph shown at 306 illustrates the weather forecast data, bias corrected weather forecast data according to the bias correction described above, and observed temperature (actual sensor data). The above algorithm or formula may be employed at 110 in FIG. 1 to correct bias in weather forecast data before using the data in VBD and VBE models.

Also as shown at 108 in FIG. 1, outlier data from historical data may be detected and removed for model calibration. For instance, when the observations are outside a certain range (e.g., 102, 104 in FIG. 1), then this observation is classified as outlier data and discarded for the further model fitting.

Under linear model assumption used in VBD model or VBE model, the 100(1-$\alpha$) % prediction interval for a single future response is $$\hat{y}_t \pm t_{t-p,\alpha/2} \hat{\sigma} \sqrt{1 + x'_t (X'_{1:(t-1)} X_{1:(t-1)})^{-1} x_t}$$

where $\hat{y}_t$ represents the fitted value of the model for time period t;

$t_{t-p,\alpha/2}$ represents the critical value of student t distribution for probability $\alpha/2$ with degree of freedom t-p;

p represents the number of weather condition information used for model fitting;

$\hat{\sigma}$ represents the standard deviation parameter estimated from the fitted linear model;

$x_t$ represents the measured weather condition available at time period t;

$X_{1:(t-1)}$ represents the collection of weather condition up to time period t-1;

$x'_t$ and $X_{1:(t-1)}'$ represent the transpose vector and matrix of $x_t$ and $X_{1:(t-1)}$, respectively;

$(X_{1:(t-1)}'X_{1:(t-1)})^{-1}$ denotes the inverse of the matrix $(X_{1:(t-1)}'X_{1:(t-1)})$.

If $y_t$, the actual observation for time period t, falls outside of this interval, a system failure alarm may be issued to a system, and the flagged energy readings may be discarded from further fitting.

Data window period for model fitting may be automatically 'compensated' with additional past data when a data point is discarded. E.g., original training period may include data from April 1 to April 30. Suppose data from April 15 and April 16 are flagged to be system failure. The training period may be extended to March 30 to April 30 (which includes data from March 30 and March 31, to compensate for the removed data of April 15 and April 16.

Figure 4:
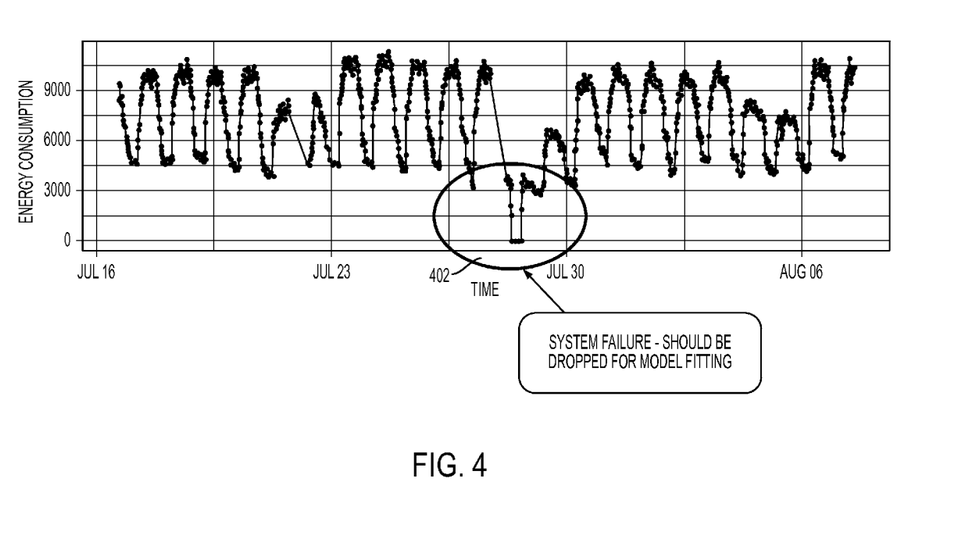
FIG. 4 shows a plot of example energy consumption data recorded or monitored by a system that monitors or records such data.

FIG. 4 shows a plot of example energy consumption data recorded or monitored by a system that monitors or records such data. Possible failure of the system on one or more days may produce data that is out of range (e.g., shown within an oval at 402) with respect to the rest of the historic recorded data. Using the data recorded during the system failure may adversely affect the prediction model, hence the corresponding data may be discarded and not used for model fitting.

Figure 5:
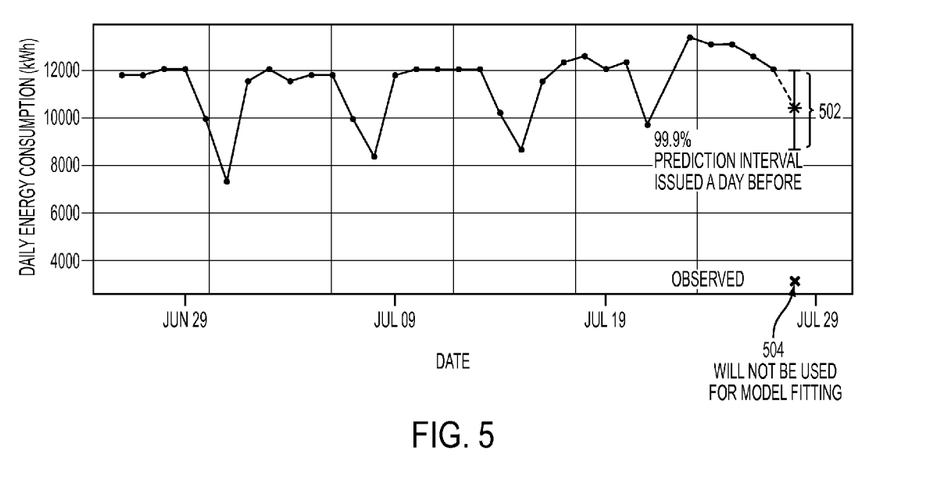
FIG. 5 shows example energy consumption data plot over a range of time period with a prediction interval issued beforehand, e.g., a day before.

FIG. 5 shows energy consumption data plot over a range of time period, along with a prediction interval issued a time period (e.g., day) ahead before. The data points represent actual energy consumption, and based on these energy consumption data, a next time period's (e.g., the next day's) energy consumption can be predicted with a prediction interval, e.g., a day ahead (e.g., shown at 502). When the next time (e.g., day) comes, the actual energy consumption data is observed. If the actual observed data falls outside of this predicted interval (e.g., shown at 504), that data will be considered as an outlier, and not used for model fitting subsequently.

Model performance evaluation and choice at 120 incorporates weighted method that combines dynamically weighted VBD and VBE model results. An example weighted forecasting is formulated as follows:

$$\hat{Y}_{new} = \Sigma_k w_k \hat{Y}_k$$

where $\hat{Y}_{new}$ represents a weighted result;

k represents an index that represents a model (e.g., k=1 may represent a VBD model, k=2 may represent VBE model);

$\hat{Y}_k$ represents prediction or forecast output by model k (e.g., VBD or VBE model);

$w_k$ represents a prediction weight assigned to model k.

As an example, the prediction weight, $w_k$, may be formulated as follows:

$$w_k = \frac{\frac{1}{\hat{\sigma}_k^2}}{\Sigma_k \frac{1}{\hat{\sigma}_k^2}}$$

with $$\hat{\sigma}_k^2 = \frac{1}{n_t} \sum_{t=1}^{n_t} (Y_t - \hat{Y}_{k,t})^2$$

where $\hat{\sigma}_k$ represents sigma value associated with model k;

$n_t$ represents the total number of time periods being considered;

$Y_t$ represents actual consumption data at time period t;

$\hat{Y}_{k,t}$ represents predicted energy consumption by model k at time period t.

In one embodiment of the present disclosure, the model with better prediction for the recent $n_t$ period gets more weights. For example, if t is the target date; then performances on the t-1, t-2, ... t-$n_t$ may be considered. In one aspect, the time period (e.g., t=1 to t=$n_t$) considered for computing the sigma values may include a predefined range of time period, e.g., 12 month period or other range of time period. That time period may be the most recent past time period: e.g., for predicting the next month's energy consumption, actual energy consumption data and predicted energy consumption data associated with the most recent past time periods of 12 months may be considered to compute the weights for use for predicting the next month's energy consumption. Hence, data from a moving window of past time period may be used to compute the weights used in the current prediction.

$\hat{\sigma}_k^2$ becomes larger when model k performs poorly recently, e.g., in the above formula, smaller weight $w_k$ is given. $\hat{\sigma}_k^2$ is the measure of discrepancy of the prediction compared to the actual observation. So better model has smaller $\hat{\sigma}_k^2$; worse model has larger $\hat{\sigma}_k^2$.

Assuming that available model predictions are multivariate normal with common mean with different variance, $\hat{Y}_{new}$ is the prediction based on maximum likelihood estimator.

Figure 6:
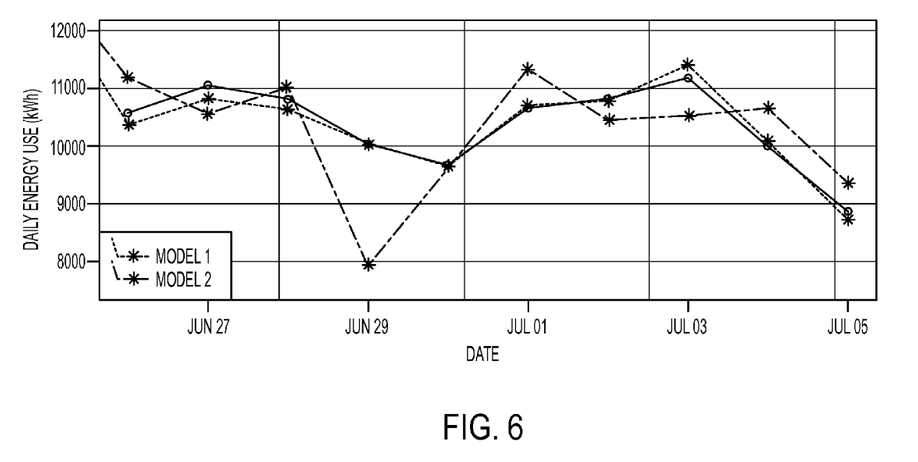
FIG. 6 is an example plot of predicted energy consumption data illustrating model weighting in one embodiment of the present disclosure.

FIG. 6 is a plot of predicted energy consumption data illustrating model weighting in one embodiment of the present disclosure. Comparing Models 1 and 2 predictions with their recent performance, measured by $$\hat{\sigma}_k^2 = \frac{1}{n_t} \sum_{t=1}^{n_t} (Y_t - \hat{Y}_{k,t})^2,$$

where $\hat{\sigma}_1^2 = 20815$, $\hat{\sigma}_2^2 = 751279$, using $$w_k = \frac{\frac{1}{\hat{\sigma}_k^2}}{\Sigma \frac{1}{\hat{\sigma}_k^2}}$$

produces $w_1 = 0.97$, $w_2 = 0.03$.

Hence, in this example, models 1 and 2 are weighted by 0.97 and 0.03, respectively. Since the methodology in one embodiment considers the record of the most recent $n_t$ days, the weights are iteratively re-calculated up to date, and therefore, dynamically weighted. For instance, the record or data associated most recent $n_t$ days may change as time moves forward, and the weights may also change.

In another one embodiment of the present disclosure, the model that performs the best recently can be picked. For example, a special weighting forecasting $\hat{Y}_{new} = \hat{Y}_k$ with the smallest $$\hat{\sigma}_k^2 = \frac{1}{n_t} \sum_{t=1}^{n_t} (Y_t - \hat{Y}_{k,t})^2$$

may be picked. For instance, the model with best recent prediction for the recent $n_t$ periods is picked. $\hat{\sigma}_k^2$ becomes larger when k-th model performs poorly recently. A model with the smallest weight is picked. In this embodiment of calculating a weight to be given to a model, the model with smallest $\hat{\sigma}_k^2$ may be given weight, $w_k=1$, and the other model with the larger $\hat{\sigma}_k^2$, given weight, $w_k=0$.

A combined VBD and VBE model with bias corrected weather forecast and outlier corrected sensor data is described above. A procedure for forecasting building energy consumption, which uses bias corrected weather forecast data, outlier corrected historic data, and the combined predictions from Variable Base Degree (VBD) and Variable Based Enthalpy (VBE) models may produce robust results. The procedure as described above may dynamically compute the relative weights of the forecast performance and make future energy predictions using the weights. Calibration performance of VBD and VBE are evaluated and weighted forecast of VBD and VBE model are used for energy forecast. Bias of weather forecast may be identified through a regression model with temporal variables by comparing historic weather forecast data and corresponding building ambient sensor data, and is corrected and inputted to the VBD model and VBE model. Outlier data in the historic data of energy consumption and ambient weather conditions are identified and removed for the calibration of VBD and VBE model. The calibration performance of VBD and VBE are evaluated using historic data, and weighted forecast of VBD and VBE model are computed as energy forecast.

Figure 7:
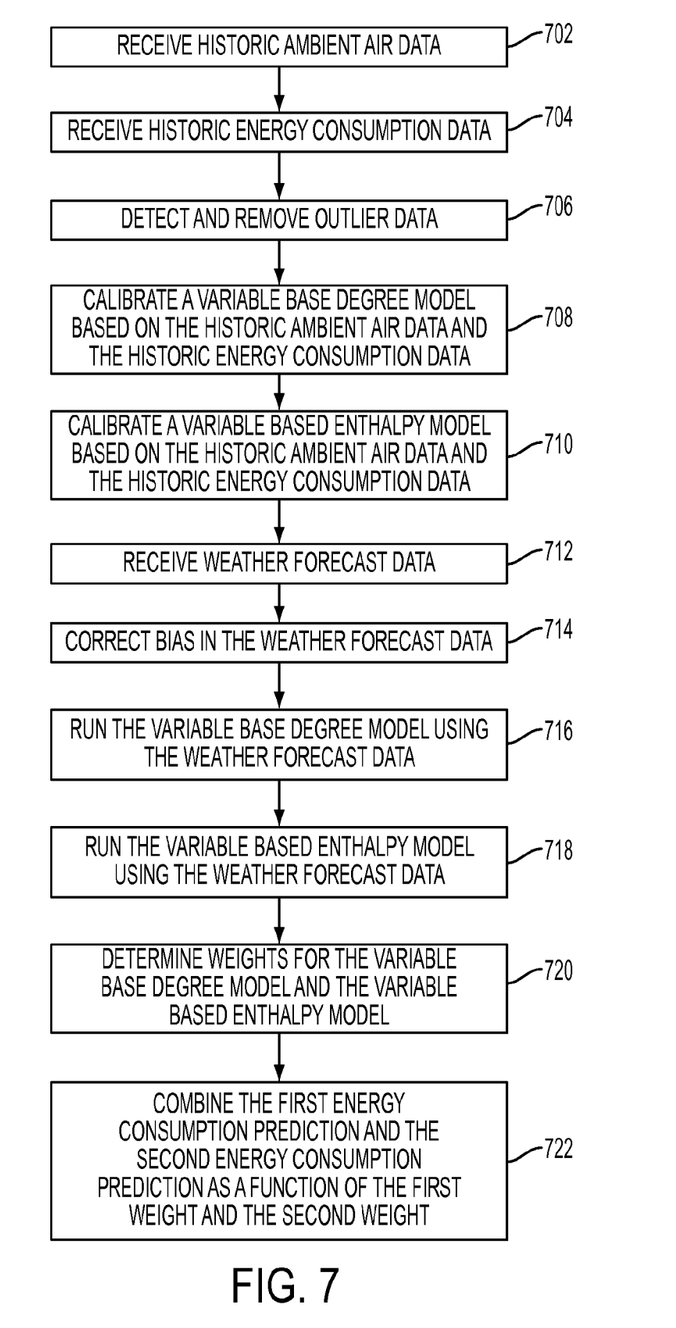
FIG. 7 is a flow diagram illustrating a method of the present disclosure in one embodiment that predicts energy consumption in a building for a future period of time.

FIG. 7 is a flow diagram illustrating a method of the present disclosure in one embodiment that predicts energy consumption in a building. At 702, historic ambient air data is received. This data may include ambient air temperature data outside the building, e.g., recorded by sensors located outside the building and/or by other mechanism. The data may be of the past time periods (e.g., past year, past months, etc. of ambient air temperature outside the building). At 704, historic energy consumption data is received. Historic energy consumption data indicates how much energy was consumed in the building, for example, recorded by one or more meters in the building. The historic energy consumption data may be received or obtained for the same past time periods (e.g., past year, past months, etc.).

At 706, outlier data from the historic ambient air data and/or the historic energy consumption data may be detected and removed, e.g., as described above with reference to FIG. 1 at 108.

At 708, based on the historic ambient air data (e.g., with the outlier data removed) and the historic energy consumption data (e.g., with the outlier data removed), a variable base degree model may be calibrated. For example, the model parameters are estimated using the historic data.

At 710, based on based on the historic ambient air data (e.g., with the outlier data removed) and the historic energy consumption data (e.g., with the outlier data removed), a variable based enthalpy model may be calibrated. For example, the model parameters are estimated using the historic data.

At 712, weather forecast data is received or obtained for a future period of time, the same period of time for which energy consumption in the building is to be predicted.

At 714, bias in the weather forecast data as related to the building's location may be corrected. For example, there may be some difference between the weather forecast data and the actual forecast of the weather in the location of the building. Thus, the difference (also referred to as bias or weather forecast bias) is detected and removed. In one embodiment, the bias correction may be performed as described with reference to FIG. 1 at 110.

At 716, the bias corrected weather forecast is input to the calibrated variable base degree model, which predicts energy consumption in the building for the period of time corresponding to the weather forecast. For the sake of clarity only, this prediction is referred to herein as a first energy consumption prediction. Running the variable base degree model produces the first energy consumption prediction.

At 718, the bias corrected weather forecast is input to the calibrated variable based enthalpy model, which predicts energy consumption in the building for the period of time corresponding to the weather forecast. For the sake of clarity only, this prediction is referred to herein as a second energy consumption prediction. Running the variable based enthalpy model produces the second energy consumption prediction.

At 720, weights associated with the models, variable base degree model and variable based enthalpy model, are determined. The weights are dynamically determined, e.g., by evaluating the performance of both models during a window of past time period, which may be predefined, e.g., the most recent past 12 month time period. The performance may be evaluated based on how well each model predicted the energy consumption by comparing the predicted data with the actual data, e.g., during that window of past time period. For the sake of clarity only, a weight associated with the variable base degree model is referred to herein as a first weight; a weight associated with the variable based enthalpy model is referred to herein as a second weight. As an example, the weights may be computed according to the formula described above with reference to FIG. 1 at 120. However, the present disclosure does not limit the weight computation solely to that formula. Thus, a methodology of the present disclosure may use another computation to compute the weights.

At 722, the first energy consumption prediction and the second energy consumption prediction are combined as a function of the first weight and the second weight. For example, the computation described above with reference to FIG. 1 at 120 may be used to compute the combination, which is output as forecasted or predicted energy consumption in the building, e.g., corresponding to the future time period of the weather forecast received at 712.

While the above description referred to two models to illustrates a methodology of the present disclosure, it should be understood that the methodology may be also applicable to more than two models. For example, energy consumption may be predicted by combining dynamically weighted results of more than two prediction models.

Figure 8:
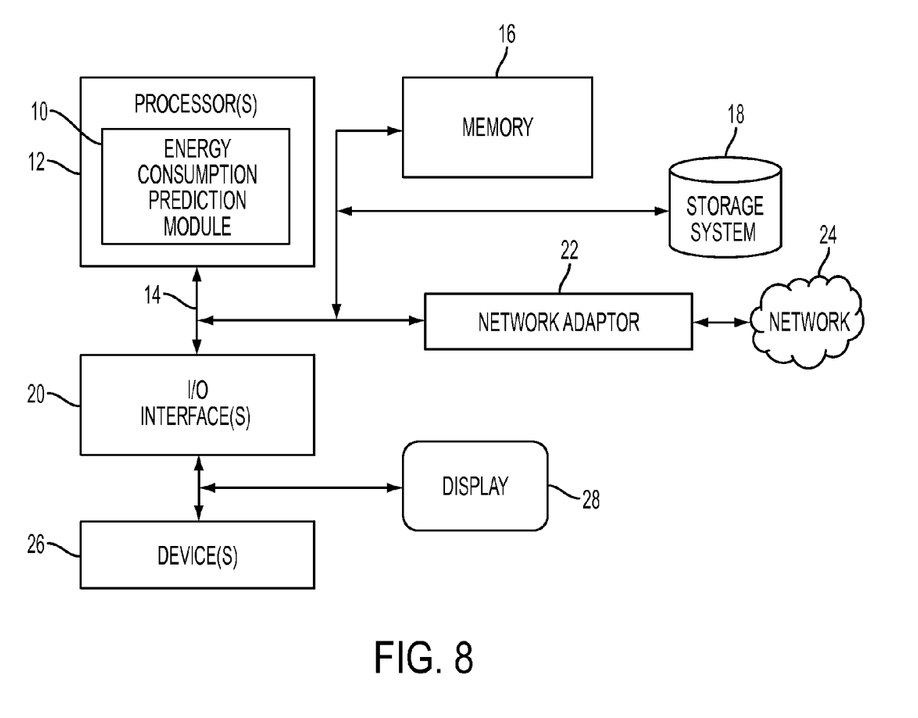
FIG. 8 illustrates a schematic of an example computer or processing system that may implement an energy consumption prediction system in one embodiment of the present disclosure.

FIG. 8 illustrates a schematic of an example computer or processing system that may implement an energy consumption prediction system in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 8 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include an energy consumption prediction module 10 that performs the methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A method of predicting energy consumption in a building, comprising:
   receiving historic ambient air data;
   receiving historic energy consumption data associated with a building;
   calibrating, by one or more hardware processors, a variable base degree model based on the historic ambient air data and the historic energy consumption data;
   calibrating, by said one or more hardware processors, a variable based enthalpy model based on the historic ambient air data and the historic energy consumption data;
   receiving weather forecast data;
   running, by said one or more hardware processors, the variable base degree model with the weather forecast data to produce a first energy consumption prediction;
   running, by said one or more hardware processors, the variable based enthalpy model with the weather forecast data to produce a second energy consumption prediction;
   computing, by said one or more hardware processors, a first weight associated with the variable base degree model dynamically based on performance of the variable base degree model and performance of the variable based enthalpy model during a predefined time period;
   computing, by said one or more hardware processors, a second weight associated with the variable based enthalpy model dynamically based on performance of the variable based enthalpy model and the variable base degree model during the predefined time period; and combining, by said one or more hardware processors, the first energy consumption prediction and the second energy consumption prediction as a function of the first weight and the second weight.

2. The method of claim 1, further comprising:
removing outlier data associated with ambient air data from the historic ambient air data; and
removing outlier data associated with energy consumption data from the historic energy consumption data.

3. The method of claim 1, further comprising:
correcting bias in the weather forecast data.

4. The method of claim 3 wherein the correcting bias in the weather forecast data comprises:
computing a regression model that formulates a relationship between previously forecasted weather data of a period of time and actual observed weather data over the same period of time; and
correcting the bias in the weather forecast data based on the relationship.

5. The method of claim 4, further comprising accounting for time dependent bias.

6. The method of claim 1, wherein the first weight and the second weight are computed as:

$$w_k = \frac{\frac{1}{\hat{\sigma}_k^2}}{\Sigma_k \frac{1}{\hat{\sigma}_k^2}}$$

with $$\hat{\sigma}_k^2 = \frac{1}{n_t} \sum_{t=1}^{n_t} (Y_t - \hat{Y}_{k,t})^2$$

where
$\hat{\sigma}_k$ represents sigma value associated with model k;
$n_t$ represents the total number of time periods being considered;
$Y_t$ represents actual consumption data at time period t;
$\hat{Y}_{k,t}$ represents predicted energy consumption by model k at time period t.

7. The method of claim 6, wherein the combining comprises:

$$\hat{Y}_{new} = \Sigma_k w_k \hat{Y}_k$$

where
$\hat{Y}_{new}$ represents a dynamically weighted combined result of the first energy consumption prediction and the second energy consumption prediction;
k represents model k;
$\hat{Y}_k$ represents energy consumption predicted by k-th model; and
$w_k$ represents weight associated with k-th model.

8. A computer readable storage medium storing a program of instructions executable by a machine to perform a method of predicting energy consumption in a building, the method comprising:
receiving historic ambient air data;
receiving historic energy consumption data associated with a building;
calibrating a variable base degree model based on the historic ambient air data and the historic energy consumption data;
calibrating a variable based enthalpy model based on the historic ambient air data and the historic energy consumption data;
receiving weather forecast data;
correcting bias in the weather forecast data;
running the variable base degree model with the weather forecast data to produce a first energy consumption prediction;
running the variable based enthalpy model with the weather forecast data to produce a second energy consumption prediction;
computing a first weight associated with the variable base degree model dynamically based on performance of the variable base degree model and performance of the variable based enthalpy model during a predefined time period;
computing a second weight associated with the variable based enthalpy model dynamically based on the performance of the variable based enthalpy model and the performance of the variable base degree model during the predefined time period; and
combining the first energy consumption prediction and the second energy consumption prediction as a function of the first weight and the second weight.

9. The computer readable storage medium of claim 8, further comprising:
removing outlier data associated with ambient air data from the historic ambient air data; and
removing outlier data associated with energy consumption data from the historic energy consumption data.

10. The computer readable storage medium of claim 8, wherein the correcting bias in the weather forecast data comprises:
computing a regression model that formulates a relationship between previously forecasted weather data of a period of time and actual observed weather data over the same period of time; and
correcting the bias in the weather forecast data based on the relationship.

11. The computer readable storage medium of claim 10, further comprising accounting for time dependent bias.

12. The computer readable storage medium of claim 8, wherein the first weight and the second weight are computed as:

$$w_k = \frac{\frac{1}{\hat{\sigma}_k^2}}{\Sigma_k \frac{1}{\hat{\sigma}_k^2}}$$

with $$\hat{\sigma}_k^2 = \frac{1}{n_t} \sum_{t=1}^{n_t} (Y_t - \hat{Y}_{k,t})^2$$

where
$\hat{\sigma}_k$ represents sigma value associated with model k;
$n_t$ represents the total number of time periods being considered;
$Y_t$ represents actual consumption data at time period t;
$\hat{Y}_{k,t}$ represents predicted energy consumption by model k at time period t.

13. The computer readable storage medium of claim 8, wherein the first weight is assigned as 1 and the second weight is assigned as 0 responsive to determining that the variable base degree model performed better than the variable based enthalpy model during the predefined time period; and wherein the second weight is assigned as 1 and the first weight is assigned as 0 responsive to determining that the variable based enthalpy model performed better than the variable base degree model during the predefined time period.

14. The computer readable storage medium of claim 8, wherein the combining comprises:

$$\hat{Y}_{new} = \Sigma_k w_k \hat{Y}_k$$

where $\hat{Y}_{new}$ represents a dynamically weighted combined result of the first energy consumption prediction and the second energy consumption prediction;

k represents model k;

$\hat{Y}_k$ represents energy consumption predicted by k-th model; and $w_k$ represents weight associated with k-th model.

15. A system for predicting energy consumption in a building, the method comprising:

a processor;

a variable base degree model calibrated by the processor based on historic ambient air data and historic energy consumption data; and a variable based enthalpy model calibrated based on the historic ambient air data and the historic energy consumption data, the processor operable to receive weather forecast data and run the variable base degree model with the weather forecast data to produce a first energy consumption prediction, the processor further operable to run the variable based enthalpy model with the weather forecast data to produce a second energy consumption prediction, the processor further operable to compute a first weight associated with the variable base degree model dynamically based on performance of the variable base degree model and the variable based enthalpy model during a predefined time period, the processor further operable to compute a second weight associated with the variable based enthalpy model dynamically based on performance of the variable based enthalpy model and the variable base degree model during the predefined time period, the processor further operable to combine the first energy consumption prediction and the second energy consumption prediction as a function of the first weight and the second weight.

16. The system of claim 15, wherein the predefined time period comprises a most recent n time periods, and wherein the predefined time period changes as time moves forward.

17. The system of claim 15, wherein the processor is further operable to remove outlier data associated with ambient air data from the historic ambient air data and remove outlier data associated with energy consumption data from the historic energy consumption data.

18. The system of claim 15, wherein the processor is further operable to correct bias in the weather forecast data.

19. The system of claim 17, wherein the processor corrects the bias in the weather forecast data by computing a regression model that formulates a relationship between previously forecasted weather data of a period of time and actual observed weather data over the same period of time, and correcting the bias in the weather forecast data based on the relationship.

20. The system of claim 18, wherein the processor further accounts for time dependent bias in the regression model.

\* \* \* \* \*